(12) United States Patent
Yarovoy et al.

(10) Patent No.: US 8,697,041 B2
(45) Date of Patent: Apr. 15, 2014

(54) ANTI-DANDRUFF COMPOSITIONS WITH CITRUS FIBERS

(75) Inventors: Yury Yarovoy, Monroe, CT (US); Georgia Shafer, Southbury, CT (US); Albert Joseph Post, Orange, CT (US)

(73) Assignee: Conopco, Inc., Englewood Cliffs, NJ (US)

( * ) Notice: Subject to any disclaimer, the term of this patent is extended or adjusted under 35 U.S.C. 154(b) by 267 days.

(21) Appl. No.: 12/853,600

(22) Filed: Aug. 10, 2010

(65) Prior Publication Data

US 2012/0040003 A1 Feb. 16, 2012

(51) Int. Cl.
*A61K 8/27* (2006.01)
*A61K 8/73* (2006.01)
*A61Q 5/02* (2006.01)
*A61Q 5/12* (2006.01)

(52) U.S. Cl.
USPC ............... 424/70.12; 424/70.13; 424/70.19; 424/642; 514/188

(58) Field of Classification Search
USPC .................. 424/70.12, 70.13, 70.19, 642
See application file for complete search history.

(56) References Cited

U.S. PATENT DOCUMENTS

| | | | |
|---|---|---|---|
| 3,085,067 A * | 4/1963 | Anderson ................. | 510/126 |
| 4,021,578 A | 5/1977 | Harich et al. | |
| 4,298,494 A | 11/1981 | Parslow et al. | |
| 5,100,573 A * | 3/1992 | Balzer ..................... | 510/535 |
| 5,308,526 A | 5/1994 | Dias et al. | |
| 5,439,682 A | 8/1995 | Wivell et al. | |
| 5,518,647 A | 5/1996 | Zocchi | |
| 5,543,074 A | 8/1996 | Hague et al. | |
| 5,648,323 A * | 7/1997 | Coffindaffer et al. ...... | 510/122 |
| 5,661,189 A | 8/1997 | Grieveson et al. | |
| 5,714,446 A | 2/1998 | Bartz et al. | |
| 5,854,293 A | 12/1998 | Glenn, Jr. | |
| 5,905,062 A | 5/1999 | Elliott et al. | |
| 5,977,038 A | 11/1999 | Birtwistle et al. | |
| 6,001,344 A | 12/1999 | Villa et al. | |
| 6,172,019 B1 | 1/2001 | Dehan et al. | |
| 6,241,812 B1 | 6/2001 | Smith et al. | |
| 6,706,258 B1 * | 3/2004 | Gallagher et al. ........... | 424/70.1 |
| 6,906,016 B1 | 6/2005 | Tsaur | |
| 7,541,320 B2 | 6/2009 | Dabkowski et al. | |
| 2003/0109391 A1* | 6/2003 | Midha et al. ................. | 510/122 |
| 2005/0031573 A1 | 2/2005 | Cho et al. | |
| 2005/0164896 A1* | 7/2005 | Dabkowski et al. .......... | 510/123 |
| 2006/0018865 A1* | 1/2006 | Aubrun-Sonneville ... | 424/70.22 |
| 2006/0105059 A1 | 5/2006 | McArthur | |
| 2006/0178288 A1 | 8/2006 | Albrecht et al. | |
| 2007/0081953 A1 | 4/2007 | Dahms | |
| 2007/0128147 A1* | 6/2007 | Schwartz et al. .......... | 424/70.31 |
| 2008/0108714 A1 | 5/2008 | Swazey et al. | |
| 2009/0269376 A1* | 10/2009 | Lundberg et al. ............. | 424/401 |
| 2009/0306223 A1 | 12/2009 | Cai et al. | |
| 2010/0009891 A1 | 1/2010 | Canto et al. | |
| 2010/0099648 A1 | 4/2010 | Debon et al. | |

FOREIGN PATENT DOCUMENTS

| | | | |
|---|---|---|---|
| CA | 2143558 | * | 8/1996 |
| EP | 0559375 A1 | | 9/1993 |
| GB | 2 208 297 A | | 3/1989 |
| WO | WO9726854 | | 7/1997 |
| WO | 2007/003391 A1 | | 1/2007 |
| WO | 2008/046753 A1 | | 4/2008 |
| WO | 2009/101545 A1 | | 8/2009 |
| WO | 2009/158687 A1 | | 12/2009 |

OTHER PUBLICATIONS

Methocel Cellulose Ethers (Dow Technical Handbook, Published Sep. 2002, http://www.dow.com/PublishedLiterature/dh_004f/0901b8038004fa1b.pdf, accessed Jun. 19, 2012).*
Katie Bird, Mar. 16, 2010, Fiberstar to launch emulsifier alternative for personal care at in-cosmetics, CosmeticsDesign.Com.
International Search Report PCT/EP2011/063196 dated Feb. 28, 2012.

* cited by examiner

*Primary Examiner* — Richard Schnizer
*Assistant Examiner* — Alma Pipic
(74) *Attorney, Agent, or Firm* — Karen E. Klumas

(57) ABSTRACT

A shampoo composition is described which includes from 1 to 25% by weight of mild surfactants, from 0.001 to 5% by weight of citrus fibers, from 0.01 to 5% by weight of anti-dandruff zinc salts, and a cosmetically acceptable carrier. The citrus fibers help structure the composition to maintain phase stability, provide appropriate viscosity and achieve deposition of the anti-dandruff zinc salts.

10 Claims, No Drawings

ANTI-DANDRUFF COMPOSITIONS WITH CITRUS FIBERS

BACKGROUND OF THE INVENTION

1. Field of the Invention

The invention concerns a shampoo composition with improved deposition properties for anti-dandruff actives.

2. The Related Art

Many persons are victims of dandruff. The condition is manifested by little scales of dead skin formed on the scalp. White in color, the scales slough-off into the hair for an aesthetically displeasing appearance. Even more displeasing is when the little white scales are caught by the shoulder area of dark clothing. This really bothers people.

Fortunately, there are readily available remedies. Most popular are shampoos with anti-dandruff actives. Zinc pyridine thione (hereinafter "ZPT") has been a leading active for more than half a century.

An unfortunate feature of most commercially available anti-dandruff shampoos is their harshness to the scalp. They can dry, sensitize and irritate skin. Significant culprits are the ubiquitous alkyl sulfate and alkyl ether sulfate surfactants.

Milder surfactants such as sodium cocoyl isethionate can be utilized to cleanse in a non-harsh manner. Yet, mild surfactants are not always fully successful in shampoo formulations. Problems are often encountered such as phase stability, incorrect viscosity range, and interference with deposition of actives.

Structurants have traditionally been incorporated into shampoos to adjust viscosity, maintain phase stability and deposit actives such as ZPT and silicone oils.

Commercial products have utilized cationic polymers as structurants. For instance, U.S. Pat. No. 7,541,320 (Unilever) discloses a cationically modified cellulose in a cleansing system that includes alkyl ether sulfate (3 EO), cocoamidopropylbetaine and cocoamidopropylhydroxysultaine, and as a conditioning active a non-volatile silicone.

U.S. Pat. No. 4,298,494 (Lever Brothers) reports use of a cationic derivative of polygalactomannan gum to stabilize a sodium alkyl sulfate and alkyl ether sulfate surfactant system.

Another group of commercially popular structurants are the acrylic polymers, particularly those known as Carbomers. For example, U.S. Pat. No. 5,543,074 (Chesebrough-Ponds) and U.S. Pat. No. 5,977,038 (Helene Curtis) regulate silicone deposition through use of crosslinked polymers of acrylic acid, commercially available under the trademark Carbopol®. U.S. Pat. No. 6,001,344 (Unilever) utilizes structurant combinations of xanthan gum and Carbopol® for stabilizing liquid cleansing compositions. U.S. Pat. No. 6,906,016 (Unilever) reports liquid cleansers structured with soluble and water swellable starches combined with linear $C_8$-$C_{13}$ fatty acids. U.S. Patent Application Publication 2010/0009891 (Unilever) reports personal care liquid compositions formulated with a bacterially produced microfibrous cellulose as a suspending system.

It is evident that traditional structurants used in the common alkyl sulfate and alkyl ether sulfate technology do not fully address the needs for mild liquid surfactant systems. There is a particular need to deliver anti-dandruff zinc salt actives in a cleansing medium that maintains phase stability, holds appropriate viscosity and enhances deposition of actives.

SUMMARY OF THE INVENTION

A shampoo is provided which includes:
(i) from about 1 to about 25% by weight of mild surfactants;
(ii) from about 0.001 to about 5% by weight of citrus fibers;
(iii) from about 0.01 to about 5% by weight of anti-dandruff zinc salts; and
(iv) a cosmetically acceptable carrier.

DETAILED DESCRIPTION OF THE INVENTION

Now it has been found that citrus fibers promote efficient deposition of anti-dandruff zinc salts onto the scalp. Satisfactory phase stability and appropriate viscosity are other benefits achieved by use of this structurant.

Citrus fibers are obtained by extraction of peels and of vesicles in pulp from a wide variety of citrus fruits. Non-limiting examples of such fruits include oranges, tangerines, limes, lemons and grapefruit. Citrus vesicles refer to the cellulosic material contained in the inner, juice-containing portion of citrus fruit. These vesicles are sometimes also referred to as coarse pulp, floaters, citrus cells, floating pulp or pulp.

Citrus pulp is high in insoluble fibers but low in sugars. The sugars are removed by the supplier's processing of the food to leave mainly insoluble hemi cellulose. It has a "spongy microstructure". The citrus fruit (mainly lemons and limes) are dejuiced to leave the insoluble plant cell wall material and some internally contained sugars and pectin. It is dried and sieved and then washed to increase the fiber content. The refining process may entail soaking the fibers in alkali, draining and standing to soften, before shearing, refining and drying. Dried material may then be milled to obtain a powdered product. The process leaves much of the natural cell wall intact while the sugars are removed. Characteristic but not limiting properties of citrus fiber include a water binding capacity from 7 to 25 (w/w) and a total fiber content of at least about 70 weight %. Particle size of the powdered form ranges from 10 to 500 micron. Especially useful is Herbacel Plus AQ. This material is commercially available as a dried powder from Herbafoods, a Division of Herbstreith & Fox KG of Neuenburg/Wurtt, Germany.

Amounts of the citrus fiber on a dry basis for use in the present compositions may range from about 0.001 to about 5%, preferably from about 0.01 to about 3%, and optimally from about 0.04 to about 2% by weight of the composition.

A second component of compositions of this invention are anti-dandruff active zinc salts. The zinc salts may be selected from zinc pyridinethione, zinc sulfate and hydrates thereof (e.g. zinc sulfate heptahydrate), and combinations. Zinc pyridinethione, (shorthand for zinc 1-hydroxy-2-pyridinethione) advantageously may be utilized as platelet particles having an average size ranging between 0.1 to 20 micron, preferably from 0.5 to 5 micron, more preferably from 1 to 2.5 micron. Amounts of the anti-dandruff zinc salts may range from about 0.01 to about 5%, preferably from about 0.1 to about 3%, and most preferably from about 0.3 to about 2% by weight of the composition.

Additional anti-dandruff actives may be included in the compositions. Illustrative substances are octopirox (piroctone olamine), azole antimicrobials (e.g. climbazole), selenium sulfide and combinations thereof. Amounts of these materials may range from about 0.01 to about 5%, preferably from 0.1 to 3%, and optimally from about 0.3 to about 4% by weight of the composition.

Advantageously compositions herein may include one or more silicones. The silicones are conditioning agents found in dispersed or suspended particulate form. They are intended to deposit onto hair remaining behind after rinsing of the hair with water. Suitable silicone oils may include polyalkyl siloxanes, polyaryl siloxanes, polyalkylaryl siloxanes, polyether siloxane copolymers and mixtures thereof. Amino silicones are often formulated with shampoo compositions. Amino silicones are silicones containing at least one primary amine, secondary amine, tertiary amine or a quaternary ammonium group. High molecular weight silicone gums can also be utilized. Another useful type are the crosslinked silicone elastomers such as Dimethicone/Vinyl/Dimethicone Crosspolymers (e.g. Dow Corning 9040 and 9041).

Number average particle size diameters for the silicones may range from about 10 nm to about 10,000 nm, most preferably from about 100 to about 500 nm.

Advantageously the compositions of this invention may include a pre-mix of a silicone microemulsion. The microemulsion is an aqueous surfactant stabilized emulsion of silicone particles having a number average particle size ranging from about 10 nm to about 1,000 nm, preferably from about 80 to about 200 nm, and optimally from 95 to 180 nm. Particle size may be measured by means of a laser light scattering technique, using a 2600 D Particle Sizer from Malvern Instruments.

The microemulsions may be prepared by high shear mechanical mixing of the silicone and water or by emulsifying the insoluble silicone with water and an emulsifier, mixing the silicone into a heated solution of the emulsifier, or by a combination of mechanical and chemical emulsification.

Any surfactant materials either alone or in admixture may be used as emulsifiers in the preparation of the silicone microemulsions. Preferred emulsifiers include anionic substances such as alkylaryl sulphonates (such as sodium dodecylbenzene sulphate), alkyl sulphates (such as sodium lauryl sulphate), alkyl ether sulphates (such as sodium laurylether sulphate nEO, where n is from 1 to 20) and mixtures thereof. Nonionic emulsifiers may also be suitable in combination with the anionic ones or by themselves to prepare the silicone microemulsions. Amounts of the emulsifier may range from 0.1 to 50% by weight of the microemulsion. Levels of silicone in the pre-mix microemulsion may range from about 5 to about 95%, preferably from about 30 to about 50% by weight based on microemulsion. A particularly preferred silicone microemulsion is Belsil 9815 sold by Wacker Corporation. This material contains 37% silicone oil.

Amounts of the silicone in compositions where present may range from about 0.01 to about 10%, preferably from about 0.1 to about 8%, more preferably from about 0.3 to about 5% by weight of the shampoo compositions.

Compositions of the present invention will also include one or more mild surfactants. By the term "mild" is meant surfactants that allow the compositions to exhibit no higher than 80% Zein Solubilized relative to the same composition except where soap replaces the mild surfactants on an identical weight basis. Preferably the compositions will exhibit no higher than 40% Zein Solubilized, and optimally no higher than 20% Zein Solubilized relative to that of the soap formulated composition.

The Zein Test is one of the most common mildness assays evaluating the effect of surfactants on proteins. It measures the solubility of the water-soluble corn protein (Zein) in a solution of a cleansing base. Goette (1967) and Schwuger (1969) have shown that a surfactant's ability to solubilize Zein correlated well with the surfactant's irritation potential. See Goette, E. "Skin Compatibility of Surfactants, Based on Zein Solubility", Chem. Phys. Appl. Surface Active Subst., Proc. Int. Congr., $4^{th}$ (1967), Meeting Date 1964, 3, 83-90; and Schwuger, M. J. "Interaction of Proteins and Detergents Studied with the Model Substance Zein.", *Kolloid Zeitschrift & Zeitschrift fur Polymere* 1969, 233 (1-2), 898-905. Lower zein scores indicate a milder material. A typical procedure involves measuring the percent of dissolved Zein as follows: (i) prepare 30 g of 1% cleansing base solution; (ii) add 1.5 g Zein and mix for 1 hour; (iii) centrifuge for 30 minutes at 3000 rpm; (iv) extract the pellet, wash with water, and dry in vacuum for 24 hours or to a constant weight; (v) measure the weight of the dry pellet. The percent of Zein solubilized is calculated using the following equation: % zein solubilized=100×[1−(weight of dried pellet/1.5)].

Mild surfactants are present in the compositions as cleansers. These may be selected from the group consisting of anionic, nonionic, cationic, amphoteric and zwitterionic type surfactants.

Illustrative but not limiting mild surfactants suitable for the present invention include the $C_{10}$-$C_{18}$ alkanoyl isethionate salts most prominent of which are cocoyl isethionate salts. Also suitable are $C_{10}$-$C_{20}$ sarcosinate salts, most preferably lauryl sarcosinate salts, and $C_{10}$-$C_{18}$ alkanoyl glycinate salts (e.g. cocoyl glycinate salts), $C_{10}$-$C_{18}$ amphoacetate and diamphoacetate salts (e.g. cocoamidopropyl amphoacetate salt), and mixtures thereof. The term "salts" mean the indicated surfactant which has a counterion selected from sodium, potassium, ammonium and triethanolammonium cations. Amounts of the mild surfactants may range in total from about 1 to about 25%, preferably from about 4 to about 20%, more preferably from about 10 to about 15% by weight of the composition.

Advantageously compositions herein may be free of alkyl sulfates and alkyl ether sulfates. By the term "free" is meant amounts of these surfactants limited to concentrations between 0 and 2%, more preferably between 0 and 1%, still more preferably between 0 and 0.5%, and optimally essentially 0% by weight of these surfactants.

Cationic polymers may be present as adjunct deposition aids. Cationic polymers useful herein are those having an average molecular weight of at least about 5,000, typically from about 10,000 to about 10 million, preferably from about 100,000 to about 2 million. Suitable cationic polymers include, for example, copolymers of vinyl monomers having cationic amine or quaternary ammonium functionalities with water soluble spacer monomers such as acrylamide, methacrylamide, alkyl and dialkyl acrylamides, alkyl and dialkyl methacrylamides, alkyl acrylate, alkyl methacrylate, vinyl caprolactone, and vinyl pyrrolidone. Other suitable spacer monomers include vinyl esters, vinyl alcohol (made by hydrolysis of polyvinyl acetate), maleic anhydride, and mixtures of all the aforementioned monomers. Other suitable cationic polymers useful herein include, for example, cationic celluloses, cationic starches, and cationic guar gums.

Illustrative are such materials as polyquarternium-10 (supplied under the brand Polymer JR 400) and guar hydroxypropyl trimonium chloride (sold under the brand Jaguar C17 and Jaguar C13S).

The cationic polymer can be included in the compositions at a level of from about 0.001% to about 10%, preferably up to about 5% by weight of the composition.

Fatty acids often are present. These may be found in amounts from about 0.1 to about 10% by weight of the compositions. Illustrative are lauric acid, palmitic acid, oleic acid, stearic acid and combinations thereof.

A primary cosmetic carrier for materials of the composition is water. Amounts of water may range from about 10% to about 95%, preferably from about 50% to about 90%, optimally from about 60 to about 85% by weight of the composition. The compositions may be emulsions wherein the systems are water-in-oil, oil-in-water or triplex water-oil-water systems.

A variety of adjunct ingredients may also be included. These can be selected from antimicrobials, fragrances, colorants, opacifiers, humectants, waxes, foam stabilizers, sunscreens, pearlizing agents, plant extracts, vitamins, organic solvents, electrolytes, sequestering agents and combinations thereof. The total amount of the auxiliaries is, for example, 0.0001 to 15% by weight, preferably from about 0.01 to 10% by weight.

Compositions of the invention advantageously are liquids having viscosities ranging from 4,000 to 30,000 cps, but preferably from 5,000 to 10,000 cps. These viscosities are measured on a Brookfield viscometer at 25° C. and 20 rpm using an N4 spindle.

All documents referred to herein, including all patents, patent applications, and printed publications, are hereby incorporated by reference in their entirety in this disclosure.

The term "comprising" is meant not to be limiting to any subsequently stated elements but rather to encompass non-specified elements of major or minor functional importance. In other words the listed steps, elements or options need not be exhaustive. Whenever the words "including" or "having" are used, these terms are meant to be equivalent to "comprising" as defined above.

Except in the operating and comparative examples, or where otherwise explicitly indicated, all numbers in this description indicating amounts of material ought to be understood as modified by the word "about".

It should be noted that in specifying any range of concentration or amount, any particular upper concentration can be associated with any particular lower concentration or amount.

EXAMPLES 1-5

A series of compositions were prepared to contrast different thickeners against the citrus fibers performance relative to deposition, rheology and stability properties. Formulas and results are recorded in Table I.

TABLE I

| Component | Example No. (Weight %) | | | | |
|---|---|---|---|---|---|
| | 1 | 2 | 3 | 4 | 5 |
| Sodium Cocoyl Glycinate | 4.0 | 4.0 | 4.0 | 4.0 | 4.0 |
| Sodium Cocoyl Isethionate/Fatty Acids | 2.0 | 2.0 | 2.0 | 2.0 | 2.0 |
| Sodium Lauryl Sarcosinate | 2.0 | 2.0 | 2.0 | 2.0 | 2.0 |
| Cocamidopropylbetaine | 4.8 | 4.8 | 4.8 | 4.8 | 4.8 |
| Silicone Microemulsion[1] | 3.0 | 3.0 | 3.0 | 2.0 | 3.0 |
| Jaguar C17 ® (quaternized guar gum) | 0.25 | 0.25 | 0.25 | 0.25 | 0.25 |
| Zinc Actives[2] | 1.0 | 1.0 | 1.0 | 1.1 | 1.0 |
| Citrus Fibers[3] | — | — | 1.5 | 1.75 | — |
| PureGel ® 990[4] | 8 | — | — | — | — |
| Aculyn ®[5] | — | 1.25 | — | — | — |
| Carb ETD 2020 | — | — | — | — | 1.0 |
| Water | to 100 | to 100 | to 100 | to 100 | to 100 |
| pH | 7.0 | 7.0 | 7.0 | 7.0 | 7.0 |
| Phase Stability[6] | No | Yes | Yes | Yes | Yes |
| Rheology[7] | 2500 | 2920 | 6040 | 6550 | 2600 |

TABLE I-continued

| Component | Example No. (Weight %) | | | | |
|---|---|---|---|---|---|
| | 1 | 2 | 3 | 4 | 5 |
| Deposition | | | | | |
| Silicone (ppm avg.) | 1265 | 158 | 1250 | 522.0 | 180 |
| Zinc (ppm avg.) | 329.5 | 132.1 | 193.5 | 172.0 | 124.6 |

[1]Silicone emulsion is Belsil 9815 (Wacker Corp.) (37% silicone pre-emulsified in water) dosed to deliver 3% active silicone oil.
[2]Ex. 4 is a mixture of zinc pyridinethione and zinc sulphate heptahydrate in respective 1.0% and 0.1% amount. All other examples have only zinc pyridinethione.
[3]Activated using high pressure homogenizer.
[4]Sodium Hydroxypropyl Starch Phosphate (Grain Processing Corp.).
[5]Acrylates/Steareth-20 Methacrylate Crosspolymer (Lubrizol Corp.).
[6]Four weeks stability test at 50° C.
[7]Viscosity measured using Brookfield viscometer at 25° C. and 20 rpm using spindle N5; the required range is from 5,000 to 10,000 cps.

Examples 3 and 4 with citrus fibers are illustrative of the present invention. Phase stability, rheology and zinc deposition were all satisfactory. Examples 1, 2 and 5 were formulated with other commercially available thickeners. Example 1 exhibited phase separation. Examples 1, 2 and 5 had viscosity below the acceptable range. Examples 2 and 5 were also inferior on zinc and silicone deposition.

Deposition Test Procedure for Zinc Actives

A sheet of artificial skin was divided into 20 pieces with a size of 5×5 cm. The pre-cut artificial skin was placed over one side of a smaller diameter X-Ray Fluorescence (XRF) instrument ring. The larger of the rings was pushed on top of the smaller one so as to fit snugly and combine the two together. Rough topography of the artificial skin was arranged to face towards the rings.

A 0.2 ml solution of ZnPTO used as a standard was added to 0.25 g of artificial skin surface. This achieved a deposition of 625 ppm onto the skin surface. Reference stock solutions were then prepared by dilution of the 625 ppm ZnPTO in chloroform to achieve a range in 50 ppm increments (from 0 to 500 ppm) reference standards. Five replicates were prepared for each concentration.

Into the XRF plastic cup were placed 1.5 ml of distilled water and 0.5 ml of the shampoo sample. The sample was stirred and rubbed onto the surface of the artificial skin with a stirring rod for 30 seconds. Thereafter, all of the shampoo sample solution was removed by suction through a plastic eye dropper. Distilled water (2 ml) was used to rinse the artificial skin. The XRF plastic cups were then left to dry naturally over night. The samples were placed in clean polyethylene bags and thereupon were ready for XRF analysis.

Deposition Procedure for Silicone

Calculations were based on dosing 1 ml of fluid on virgin hair switches. DC 200 silicone was dispersed into water using a calibration curve ranging in silicone ppm from 0 to 6,000 in water to form stock solutions.

Switches were dried (at 50° C.) in a drying cabinet overnight) and cooled, then mounted on pre-weighed 40 mm XRF cells. Each cell was weighed and then the switch mounted in the center of the XRF cell; this ensured that the complete width of the switch was placed in the cell. The switch was then trimmed and both switch and cell weighed together again to allow calculation of the actual hair, and hence, exact dosed amount.

Switches were pre-soaked in 14% sodium lauryl ether sulfate (1 EO) solution for 30 minutes and rinsed thoroughly. A sample of 1.25 ml of shampoo was added to five hair switches and then washed for 30 seconds. They were then rinsed under a pre-set water flow (40° C. and 3-4 liters/minute) for 30 seconds. The washing step was then repeated but the rinse was raised to 60 seconds. The switch was combed through and dried at 50° C. for one hour. Thereafter, the switch was mounted and combed until flat aligned fibers were obtained. Care was taken to ensure that the complete width of the switch was mounted on the cell and clamped to secure the switch between the cell parts. The cells were then placed in plastic bags and submitted for XRF analysis.

EXAMPLES 6-10

Shampoo compositions according to the present invention are further illustrated in the Examples under Table II.

TABLE II

| Component | Example No. (Weight %) | | | | |
|---|---|---|---|---|---|
| | 6 | 7 | 8 | 9 | 10 |
| Sodium Cocoyl Glycinate | 6.0 | — | 3.0 | 2.0 | — |
| Sodium Cocoyl Isethionate | 1.8 | 8.0 | 2.5 | 1.0 | 12.5 |
| Fatty Acids | 0.3 | 0.3 | 0.3 | 0.3 | 0.3 |
| Sodium Lauryl Sarcosinate | — | — | 3.0 | 3.0 | — |
| Cocamidopropylbetaine | — | — | — | 2.0 | 2.0 |
| Silicone Oil | 1.0 | 1.0 | 1.0 | 1.0 | 1.0 |
| Jaguar C17 ® (quaternized guar gum) | 0.25 | 0.25 | 0.25 | 0.25 | 0.25 |
| Zinc Pyridinethione/Zinc Sulfate | 1.0 | 1.0 | 1.0 | 0.8 | 2.5 |
| Silicone Microemulsion | 3.0 | 3.0 | 2.0 | 2.0 | 2.0 |
| Citrus Fibers | 1.75 | 2.25 | 3.0 | 3.0 | 3.5 |
| Water | to 100 | to 100 | to 100 | to 100 | to 100 |

The foregoing description illustrates selected embodiments of the present invention. In light thereof, variations and modifications will be suggested to one skilled in the art, all of which are within the spirit and purview of this invention.

What is claimed is:

1. A shampoo composition comprising:
   (i) from about 1 to about 25% by weight of mild surfactants comprising cocoyl glycinate salts and free of alkyl sulfates and alkyl ether sulfates which are limited to amounts between 0 and 1% by weight of the composition;
   (ii) from about 0.04 to about 5% by weight of citrus fibers;
   (iii) from about 0.01 to about 5% by weight of anti-dandruff zinc salts;
   (iv) from about 0.1 to about 10% by weight of a silicone microemulsion provided to the composition as a pre-mix in water, the silicone being present in a number average particle size ranging from 80 to 200 nm;
   (v) a cosmetically acceptable carrier; and
   wherein the composition exhibits no higher than 80% Zein Solubilized in a Zein Test and a viscosity, measured at 25° C. and 20 rpm with a Brookfield viscometer using spindle N5, of from 5,000 to 10,000 cps.

2. The shampoo composition according to claim 1 further comprising mild surfactants selected from the group consisting of cocoyl isethionate salts, lauryl sarcosinate salts and combinations thereof.

3. The shampoo composition according to claim 1 wherein the antidandruff zinc salts are selected from the group consisting of zinc pyridinethione, zinc sulfate and hydrates thereof, and combinations thereof.

4. The shampoo composition according to claim 1 further comprising from about 4% to about 20% by weight of cocoamidopropylbetaine.

5. The shampoo composition according to claim 1 wherein the alkyl sulfates and alkyl ether sulfates range in an amount between 0 and 0.5% by weight of the composition.

6. The shampoo composition according to claim 1 wherein the citrus fibers have a particle size ranging from 10 to 500 micron.

7. The shampoo according to claim 1 wherein the citrus fibers are present in an amount from about 1.5 to about 2% by weight of the composition.

8. The shampoo according to claim 1 wherein the anti-dandruff zinc salts are present in an amount from about 0.3 to about 2% by weight of the composition.

9. A method for depositing anti-dandruff zinc salts and silicone from a shampoo composition onto hair, the method comprising:
   (A) obtaining a composition comprising:
      (i) from about 1 to about 25% by weight of mild surfactants comprising cocoyl glycinate salts and free of alkyl sulfates and alkyl ether sulfates which are limited to amounts between 0 and 1% by weight of the composition;
      (ii) from about 0.04 to about 5% by weight of citrus fibers;
      (iii) from about 0.01 to about 5% by weight of anti-dandruff zinc salts;
      (iv) from about 0.1 to about 10% by weight of a silicone microemulsion provided to the composition as a pre-mix in water, the silicone being present in a number average particle size ranging from 80 to 200 nm;
      (v) a cosmetically acceptable carrier; and
      wherein the composition exhibits no higher than 80% Zein Solubilized in a Zein Test and a viscosity, measured at 25° C. and 20 rpm with a Brookfield viscometer using spindle N5, of from 5,000 to 10,000 cps; and
   (B) applying the shampoo composition to the hair to obtain deposition of the anti-dandruff zinc salts and silicone onto the hair.

10. The method according to claim 9 wherein the citrus fibers have a particle size ranging from 10 to 500 microns.

* * * * *